(12) United States Patent
Greene

(10) Patent No.: US 9,545,509 B2
(45) Date of Patent: Jan. 17, 2017

(54) LEAD FIXATION DEVICE FOR SECURING A MEDICAL LEAD IN A HUMAN PATIENT

(75) Inventor: David Greene, Fort Wayne, IN (US)

(73) Assignee: NeuroPace, Inc., Mountain View, CA (US)

( * ) Notice: Subject to any disclaimer, the term of this patent is extended or adjusted under 35 U.S.C. 154(b) by 177 days.

(21) Appl. No.: 13/310,695

(22) Filed: Dec. 2, 2011

(65) Prior Publication Data

US 2012/0143297 A1    Jun. 7, 2012

Related U.S. Application Data

(60) Provisional application No. 61/419,755, filed on Dec. 3, 2010.

(51) Int. Cl.
*A61N 1/05* (2006.01)
*A61N 1/375* (2006.01)

(52) U.S. Cl.
CPC ............ *A61N 1/0539* (2013.01); *A61N 1/05* (2013.01); *A61N 1/0526* (2013.01); *A61N 1/0529* (2013.01); *A61N 1/0534* (2013.01); *A61N 1/0558* (2013.01); *A61N 1/375* (2013.01)

(58) Field of Classification Search
CPC ...... A61N 1/0539; A61N 1/05; A61N 1/0558; A61N 1/059; A61N 1/0526
USPC .......................................... 607/116
See application file for complete search history.

(56) References Cited

U.S. PATENT DOCUMENTS

| | | | |
|---|---|---|---|
| 4,328,813 A | 5/1982 | Ray | |
| 5,464,446 A * | 11/1995 | Dreessen | A61M 39/0247 604/175 |
| 5,843,150 A | 12/1998 | Dreessen et al. | |
| 5,865,842 A | 2/1999 | Knuth et al. | |
| 5,865,843 A | 2/1999 | Baudino et al. | |
| 5,927,277 A | 7/1999 | Baudino et al. | |
| 6,044,304 A * | 3/2000 | Baudino | A61N 1/0539 600/378 |
| 6,134,477 A | 10/2000 | Knuteson et al. | |
| 6,210,417 B1 | 4/2001 | Baudino et al. | |
| 6,319,241 B1 | 11/2001 | King et al. | |
| 6,321,104 B1 | 11/2001 | Gielen et al. | |
| 6,795,737 B2 | 9/2004 | King et al. | |

(Continued)

FOREIGN PATENT DOCUMENTS

WO    0176498    10/2001
WO    2004103468    12/2004

*Primary Examiner* — Michael Kahelin
*Assistant Examiner* — Minh Duc Pham
(74) *Attorney, Agent, or Firm* — David S. Sarisky; Loza & Loza, LLP

(57) ABSTRACT

A lead fixation device for securing a medical lead in a human patient includes: a single-piece structure comprising: a top surface; a bottom surface; an outer perimeter; and an inner perimeter, the inner perimeter comprising: a diameter approximately equal to or smaller than a diameter of a burr hole into which the lead fixation device is designed to be deployed; a central bore extending longitudinally from the top surface through to the bottom surface, a portion of the central bore being located in approximately a center of the lead fixation device and comprising a central bore diameter; and at least one retention tract formed in the top surface of a cap of the lead fixation device, the retention tract configured for retaining, with an interference fit, a portion of a body of the medical lead in the lead fixation device.

19 Claims, 16 Drawing Sheets

(56) References Cited

U.S. PATENT DOCUMENTS

| | | |
|---|---|---|
| 6,810,285 B2 | 10/2004 | Pless et al. |
| 6,902,569 B2 | 6/2005 | Parmer et al. |
| 7,204,840 B2 | 4/2007 | Skakoon et al. |
| 7,235,084 B2 | 6/2007 | Skakoon et al. |
| 7,580,756 B2 | 8/2009 | Schulte et al. |
| 7,604,644 B2 | 10/2009 | Schulte et al. |
| 7,636,596 B2 | 12/2009 | Solar |
| 7,637,915 B2 | 12/2009 | Parmer et al. |
| 7,660,621 B2 | 2/2010 | Skakoon et al. |
| 7,704,260 B2 | 4/2010 | Skakoon et al. |
| 7,744,606 B2 | 6/2010 | Miller et al. |
| 7,766,394 B2 | 8/2010 | Sage et al. |
| 7,815,651 B2 | 10/2010 | Skakoon et al. |
| 7,828,809 B2 | 11/2010 | Skakoon et al. |
| 7,833,231 B2 | 11/2010 | Skakoon et al. |
| 7,857,820 B2 | 12/2010 | Skakoon et al. |
| 7,949,410 B2 | 5/2011 | Rodriguez |
| 7,976,530 B2 | 7/2011 | Johnson et al. |
| 7,988,674 B2 | 8/2011 | Adams et al. |
| 8,116,850 B2 | 2/2012 | Solar |
| 8,152,792 B1 | 4/2012 | Kornel |
| 8,192,445 B2 | 6/2012 | Parmer et al. |
| 8,845,656 B2 | 9/2014 | Skakoon et al. |
| 8,911,452 B2 | 12/2014 | Skakoon et al. |
| 2005/0182421 A1 | 8/2005 | Schulte et al. |
| 2005/0182422 A1 | 8/2005 | Schulte |
| 2005/0182424 A1 | 8/2005 | Schulte et al. |
| 2005/0182425 A1* | 8/2005 | Schulte ............... A61N 1/0539 606/130 |
| 2009/0112327 A1 | 4/2009 | Lane et al. |
| 2009/0306750 A1* | 12/2009 | Boling ............... A61N 1/0531 607/116 |
| 2009/0326610 A1 | 12/2009 | Pless et al. |
| 2010/0179563 A1 | 7/2010 | Skakoon et al. |
| 2010/0312193 A1 | 12/2010 | Stratton |
| 2011/0270187 A1* | 11/2011 | Nelson ............... A61M 25/02 604/151 |
| 2013/0066410 A1 | 3/2013 | Funderburk |

* cited by examiner

LEAD FIXATION DEVICE FOR SECURING A MEDICAL LEAD IN A HUMAN PATIENT

REFERENCE TO RELATED APPLICATIONS

This application claims priority to and benefit of U.S. Provisional Patent Application 61/419,755 filed Dec. 3, 2010, assigned to the assignee of the present application, which is incorporated herein, in its entirety, by reference.

The issued U.S. Pat. No. 6,810,285, entitled "Seizure Sensing and Detection Using an Implantable Device" by Pless et al., filed Jun. 28, 2001 and issued Oct. 26, 2004, co-owned by and assigned to the assignee of the present invention, is hereby incorporated by reference as background material. The co-pending U.S. patent application Ser. No. 12/554,959, entitled "Systems and Methods for Interacting with an Implantable Medical Device" by Pless, at al., filed Sep. 7, 2009, co-owned by and assigned to the assignee of the present invention, is hereby incorporated by reference as background material.

FIELD OF THE INVENTION

Embodiments generally relate to devices and methods of using those devices that control the movement of leads after they have been implanted at a desired site in a patient's body. More particularly, the disclosed embodiments relate to devices and methods for affixing a lead within a burr hole that is formed in a patient's skull to gain access to the brain.

BACKGROUND

Neurostimulation systems, and increasingly implantable neurostimulation systems, are used to treat various neurological diseases and other neurological disorders, such as epilepsy, movement disorders (e.g., Parkinson's disease) and chronic pain. Research is ongoing concerning use of implantable neurostimulation systems to treat psychological disorders (e.g., depression), headaches and Alzheimer's disease and to facilitate stroke recovery.

A typical neurostimulation system comprises a stimulation source, such as a pulse generator, that provides stimulation to target neural tissue via one or more leads connected to the stimulation source. Each lead has one or more electrodes designed to be placed on a surface of the brain (cortical electrodes) or within the brain (deep brain electrodes). A signal is transmitted from the stimulation source to the electrode(s), and thus to the desired site in the brain. Some systems also have the capacity to detect and respond to signals detected from one or more of the electrodes through the leads (e.g., "responsive neurostimulators" or other "closed-loop" devices).

Access to the desired portion of the brain is commonly achieved by drilling a hole in a patient's skull (cranium). A cranial drill, sometimes referred to as a "burr", is used to drill the hole through the outer table, cancellous bone, and inner table of the cranium.

A lead with one or more electrodes on its distal end is introduced into the burr hole and manipulated from outside the patient until the electrodes are positioned at the desired location. Leads with cortical strip electrodes are designed to lay on a surface of the brain. The location at which a cortical strip electrode is placed, for example, may correspond to an area of brain tissue which has previously been identified as the likely focus of seizure activity, for example, using magnetic resonance imaging or some other diagnostic or clinical procedure. Leads with deep brain electrodes are designed to be pushed at least partly into the brain tissue, so that the electrodes rest at or near a target structure (e.g., hypothalamus, subthalamic nucleus, etc.).

Maintaining the electrodes at the desired location once the leads have been implanted is often important relative to the purpose of the implant (e.g., delivering stimulation therapy, monitoring a sensed brain signal, etc.). Thus, once one or more leads are placed in the desired areas on in the brain, the proximal portions of the leads (i.e., a portion of each lead that extends away from the implant site and exteriorly of the burr hole) commonly are secured to prevent the electrodes from being inadvertently dislodged or otherwise moving too much from the location at which the distal ends of the leads bearing the electrodes have been placed. One or all of the components that are used to secure the leads at the site of the burr hole commonly are put into place in the burr hole before the leads are implanted.

Sometimes, the leads are permitted some play or give after they have been secured, to allow for some relative movement of the leads and the brain or skull, for example, during some sort or head trauma. A device used to secure the proximal portions of the leads also often is provided with a feature that allows the hole to be sealed or substantially sealed to minimize infection from outside agents, such as a cap with a slot through which the leads can be extended and then routed to measuring or stimulation components.

Lead fixation devices commonly are comprised of multiple parts that are assembled in the operating room by the surgeon, require neurosurgical screws to secure, and are made partially or wholly of rigid materials.

SUMMARY

Embodiments described herein disclose a single piece lead fixation device that is pressed directly into a standard sized burr hole and that does not require neurosurgical screws to secure it to the cranium. Embodiments enable a medical lead to be securely held in place in a retention track via an interference fit, using a combination of materials varying in stiffness. Further and as will be described herein, a longitudinal slit within the lead fixation device provides more positioning choices with regards to the medical lead (e.g., positioning the medical lead at an edge of the burr hole). Moreover, embodiments provide various devices and methods for securing retaining a seal in a burr hole, without using neurological screws.

Embodiments can be described as follows:

A method for fixing a medical lead relative to a burr hole formed in a human patient using a lead fixation device, the method comprising: aligning a lead fixation device relative to a distal end of a cannula, the cannula configured for facilitating implanting a medical lead in the human patient, the lead fixation device having an overall mushroom-like shape and comprising: a top surface; a bottom surface; an outer perimeter; an inner perimeter; a central bore extending from the top surface through the bottom surface, the inner diameter selected to approximate an inner diameter of the burr hole, and the outer diameter selected to be at least slightly greater than the inner diameter, the central bore further provided with a diameter that is at least slightly greater than the diameter of the cannula; at least one retention tract formed in the top surface of the cap, the at least one retention tract configured for retaining a portion of the body of the medical lead in the lead fixation device with an interference fit; passing the central bore of the lead fixation device over a proximal end of the cannula; inserting a distal end of the cannula into the burr hole; inserting a distal end of the medical lead into the cannula; implanting the medical lead at a desired location in the human patient, thereby achieving an implanted medical lead; situating the lead fixation device so that the lead fixation device is adjacent to the burr hole; pressing the lead fixation device into the burr hole so that at least the bottom surface is inside the burr hole; withdrawing the cannula by advancing it proximally of the implanted medical lead and over the proximal end of the implanted medical lead; selecting one of the at least one retention tract into which to place a portion of the body of the medical lead, thereby achieving a selected retention tract; placing the portion of the body of the medical lead that extends proximally out of the burr hole and out of the central bore onto the selected retention tract; and pressing the portion of the body of the medical lead placed in the selected retention tract further into the selected retention tract to secure it with an interference fit.

Further, embodiments include: wherein the at least one retention tract provided in the lead fixation device further comprises a trough formed in the top surface having a generally semicircular cross-section, the semicircular cross section having a radius approximating the radius of the body of the medical lead, and wherein the pressing the portion of the body of the medical lead into the selected retention tract further comprises: pressing the body of the medical lead into the trough.

Embodiments include a method of fixing a medical lead in a burr hole formed in a cranium of a human patient, the method comprising: passing a lead fixation device over a body of a medical lead that has a proximal end and a distal end which has been implanted in a body of the patient, the lead fixation device being provided with a base and a cap formed integrally with each other such that the base and cap comprise a single-piece structure, the single-piece structure comprising: a top surface; a bottom surface; an outer perimeter; an inner perimeter, the inner perimeter having a diameter approximating a diameter of a burr hole into which the lead fixation device is designed to be deployed; a central bore extending longitudinally from the top surface through to the bottom surface, the bore being located in approximately the center of the lead fixation device and having a generally circular perimeter, the central bore comprising: a central bore diameter that is greater than a diameter of a body of the medical lead; at least one retention tract formed in the top surface of the cap, the at least one retention tract configured for retaining a portion of the body of the medical lead in the lead fixation device with an interference fit; aligning the proximal end of the medical lead with the central bore; sliding the lead fixation device over the medical lead up to the burr hole; pressing the base of the single-piece structure into the burr hole; selecting one of the at least one retention tract to achieve a selected retention tract; placing a portion of the body of the medical lead that extends proximally of the burr hole and out of the central bore into the selected retention tract; and pressing the portion of the body of the medical lead placed on the selected retention tract into the selected retention tract to secure it with an interference fit.

Further embodiments include: a method for fixing a medical lead relative to a burr hole formed in a human patient using a lead fixation device, the method comprising: aligning a lead fixation device relative to a cannula having a cannula body, the cannula configured for facilitating an implanting of a medical lead in the human patient, the lead fixation device comprising: a base and a cap formed as a single piece, the single piece comprising: a top surface; a bottom surface; an outer perimeter; an inner perimeter; a central bore extending from the top surface through the bottom surface, the inner diameter selected to approximate an inner diameter of the burr hole, and the outer diameter selected to be at least slightly greater than the inner diameter, the central bore comprising: a diameter that is at least slightly greater than the diameter of the cannula; at least one retention tract formed in the top surface of the cap, the at least one retention tract configured for retaining a portion of the body of the medical lead in the lead fixation device with an interference fit; a slit extending from the central bore through a portion of the base and the cap to the outer perimeter, the slit allowing the lead fixation device to be slid onto or off of the body of the medical lead; positioning the slit at the outer perimeter around the body of the cannula; prying the slit open from its normal resting position; sliding the lead fixation device through the slit so that the cannula is located in the central bore and the slit returns to its resting position; implanting a medical lead through the cannula so that a distal end thereof is positioned at a desired location in the human patient; situating the lead fixation device so that the lead fixation device is adjacent to the burr hole; pressing the lead fixation device into the burr hole so that at least the bottom surface is inside the burr hole, thereby achieving an implanted medical lead; withdrawing the cannula by advancing it proximally of the implanted medical lead and over the proximal end of the implanted lead; selecting one of the at least one retention tract to achieve a selected retention tract; placing a portion of the lead body extending proximally of the burr hole and out of the central bore onto the selected retention tract; and pressing the portion of the body of the medical lead placed on the selected retention tract into the selected retention tract to secure it with an interference fit.

Embodiments further include: removing a stylet provided in the medical lead to facilitate implantation of the medical lead prior to placing a portion of the body of the medical lead extending proximally of the burr hole and out of the central bore into the selected retention tract.

A method for fixing a medical lead relative to a burr hole formed in a human patient using a lead fixation device, the method comprising: aligning a lead fixation device relative to a body of a medical lead, the lead fixation device comprising: a base and cap formed as a single piece, the single piece comprising: a top surface; a bottom surface; an outer perimeter; an inner perimeter; a central bore extending from the top surface through the bottom surface, the inner diameter selected to approximate an inner diameter of the burr hole, and the outer diameter selected to be at least slightly greater than the inner diameter, the central bore having a diameter that is at least slightly greater than a diameter of the body of the medical lead; at least one retention tract formed in the top surface of the cap, the at least one retention tract configured for retaining a portion of the body of the medical lead in the lead fixation device with an interference fit; a slit extending from the central bore through a portion of the base and the cap to the outer perimeter, the slit allowing the lead fixation device to be slid onto or off of the body of the medical lead; positioning the slit at the outer perimeter around the body of the medical lead; prying the slit open from its normal resting position; sliding the lead fixation device through the slit so that the cannula is located in the central bore and the slit returns to its resting position; implanting the medical lead so that a distal end thereof is positioned at a desired location in the human patient, thereby achieving an implanted medical lead; situating the lead fixation device so that the lead fixation device is adjacent to the burr hole; pressing the lead fixation device into the burr hole so that at least the bottom surface is inside the burr hole; selecting one of the at least one retention tract to achieve a selected retention tract; placing a portion of the body of the medical lead that extends proximally of the burr hole and out of the central bore onto the selected retention tract; and pressing the portion of the body of the medical lead placed on the selected retention tract into the selected retention tract to secure it with an interference fit.

Embodiments further comprise: removing a stylet provided in the medical lead to facilitate implantation of the medical lead prior to the placing a portion of the body of the medical lead body that extends proximally of the burr hole and out of the central bore onto the selected retention tract.

Embodiments include a method of fixing a medical lead relative to a burr hole formed in a human patient using a lead fixation device comprising: aligning a lead fixation device relative to a body of the medical lead, the lead fixation device comprising: a base and cap formed as a single piece, the single piece comprising: a top surface; a bottom surface; an outer perimeter; an inner perimeter, the inner diameter selected to approximate an inner diameter of the burr hole, and the outer diameter selected to be at least slightly greater than the inner diameter; a central bore extending from the top surface through the bottom surface, the central bore having a diameter that is at least slightly greater than the diameter of the lead body; at least one retention tract formed in the top surface of the cap, the at least one retention tract adapted to retain a portion of the lead body in the lead fixation device with an interference fit; a slit extending from the central bore through a portion of the base and the cap to the outer perimeter, the slit allowing the lead fixation device to be slid onto or off of the body of the medical lead; positioning the lead fixation device so that the lead body is approximately concentric with the central bore; implanting the medical lead so that a distal end thereof is positioned at a desired location in the patient, thereby achieving an implanted medical lead; situating the lead fixation device so that the lead fixation device is adjacent to the burr hole; pressing the lead fixation device into the burr hole so that at least the bottom surface is inside the burr hole; selecting one of the at least one retention tract, thereby achieving a selected retention tract; placing a portion of the body of the medical lead that extends proximally of the burr hole and out of the central bore onto the selected retention tract; and pressing the portion of the body of the medical lead placed on the retention tract into the retention tract to secure it with an interference fit.

Embodiments include a method of fixing medical leads relative to a burr hole formed in a human patient using a lead fixation device comprising: aligning a lead fixation device relative to each body of a medical lead of a plurality of medical leads, the lead fixation device comprising: a base and cap formed as a single piece, the single piece comprising: a top surface; a bottom surface; an outer perimeter; an inner perimeter, the inner diameter selected to approximate an inner diameter of the burr hole, and the outer diameter selected to be at least slightly greater than the inner diameter; a central bore extending from the top surface through the bottom surface, the central bore having a diameter that is at least slightly greater than the aggregate diameter of the bodies of the plurality of medical leads; at least one retention tract formed in the top surface of the cap, the at least one retention tract configured for retaining a portion of each body of one or more medical leads in the lead fixation device with an interference fit; a slit extending from the central bore through a portion of the base and the cap to the outer perimeter, the slit allowing the lead fixation device to be slid onto or off of the bodies of the plurality of medical leads; positioning the lead fixation device so that the bodies of the plurality of medical leads are approximately concentric with the central bore; implanting each body of the bodies of the plurality of medical leads so that a distal end of each body of the bodies of the plurality of medical leads is positioned at a desired location in the human patient; situating the lead fixation device so that the lead fixation device is adjacent to the burr hole; pressing the lead fixation device into the burr hole so that at least the bottom surface is inside the burr hole; selecting one of the at least one retention tract for each body of the bodies of the plurality of medical leads, thereby achieving selected retention tracts; placing a portion of each body of the bodies of the plurality of medical leads that extend proximally of the burr hole and out of the central bore onto each of the selected retention tracts; and pressing each body of the bodies of the plurality of medical leads into each of the selected retention tracts to secure each body of the bodies of the plurality of medical leads to the lead fixation device with an interference fit.

Embodiments further include: wherein the lead fixation device has a first medical lead with a first body, a second medical lead with a second lead body, and a first and second retention tract, wherein the placing a portion of each body of a medical lead of the plurality of bodies of the medical leads that extend proximally of the burr hole and out of the central bore onto each of the selected retention tracts further comprises: selecting the first retention tract for the body; placing a portion of the first body onto the first retention tract; selecting the second retention tract for the second body; and placing a portion of the second body onto the second retention tract.

Embodiments include a method of fixing medical leads relative to a burr hole formed in a human patient using a lead fixation device comprising: aligning a lead fixation device relative to each lead body of a plurality of medical leads; the lead fixation device comprising: a single-piece structure formed from a first material and a second material, the first material having a stiffness that is greater than the stiffness of the second material, the single piece structure comprising: a top surface; a bottom surface; an outer perimeter, an inner perimeter, the inner perimeter having a diameter approximately equal to or smaller than a diameter of the burr hole into which the lead fixation device is designed to be deployed; a central bore extending longitudinally from the top surface through to the bottom surface, the central bore being located in approximately the center of the lead fixation device and having a generally circular perimeter, the central bore comprising: a central bore diameter; at least one retention tract formed in the top surface of the cap, the retention tract configured for retaining a portion of a body of the medical lead in the lead fixation device with an interference fit; a plurality of elements formed from the first material, the plurality of elements including an approximately C-shaped section adjacent the central bore and extending from the bottom surface towards the top surface; positioning the lead fixation device so that the body of the medical lead is approximately concentric with the central bore; implanting the medical lead so that a distal end thereof is positioned at a desired location in the human patient, thereby achieving an implanted medical lead; situating the lead fixation device so that the lead fixation device is adjacent to the burr hole; applying a compressive force to the approximately C-shaped section from a first resting position to a second under tension position; fitting the lead fixation device into the burr hole while the approximately C-shaped section is compressed; releasing the compressive force so that the approximately C-shaped section tends to return to its first resting position and the lead fixation device is secured in the burr hole with a tension fit; selecting one of the at least one retention tract for the body of the medical lead, thereby achieving a selected retention tract; placing a portion of the body of the medical lead that extends proximally of the burr hole and out of the central bore onto the selected retention tract; and pressing the portion of the body of the medical lead placed in the selected retention tracts onto the retention tracts to secure the portion of the body of the medical lead with an interference fit.

Embodiments further include, wherein the lead fixation device is further provided with first and second suture apertures, each disposed on a different side of each retention tract, each suture aperture having a size and shape adapted to accommodate at least one suture to secure the lead body in the lead fixation device; and further comprising: securing a suture through at least one of a first suture aperture and a corresponding at least one of a second suture aperture.

In further embodiments, wherein the lead fixation device is further provided with a first and a second forceps receptacle in the top surface, the first forceps receptacle disposed at a location corresponding to a first side of the approximately C-shaped section and the second forceps receptacle disposed at a location corresponding to a second side of the approximately C-shaped section, the first and second forceps receptacles extending at least part way through the top surface towards the bottom surface of the lead fixation device, wherein the applying of the compressive force to the approximately C-shaped section from the first resting position to the second under tension position further comprises: inserting a first grasping end of the forceps into one of the first forceps receptacles and a second grasping end of the forceps into a corresponding one of the second forceps receptacles and using the forceps to compress the at least one retention tract until the lead fixation device is situated in the burr hole; releasing the compressive force so that the approximately C-shaped section tends to return to its first resting position and the lead fixation device is secured in the burr hole with a tension fit, wherein the releasing comprises: removing the grasping ends of the forceps from the first and second forceps receptacles.

Figure 1:
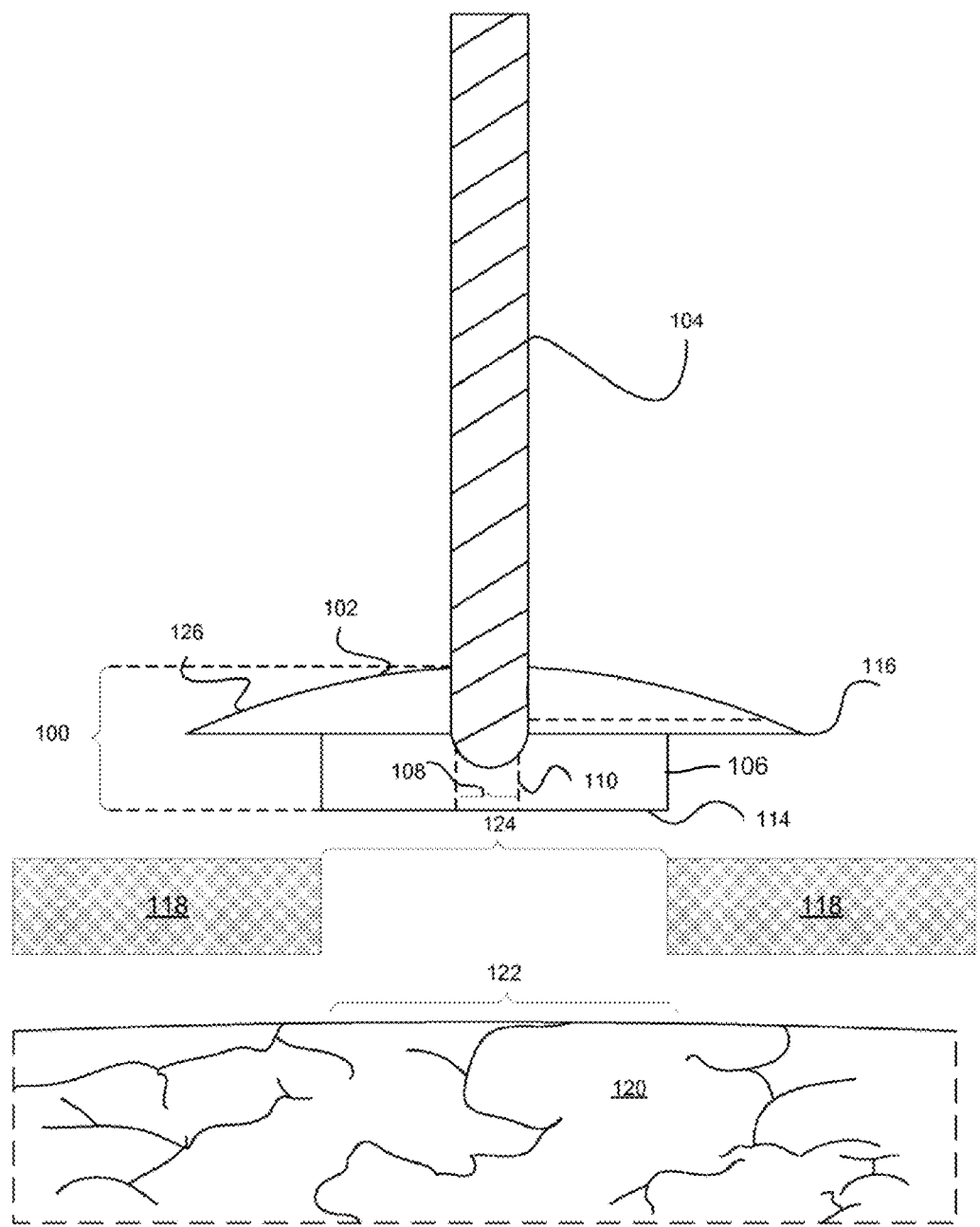
FIG. 1 is a perspective view of a lead fixation device, in accordance with an embodiment.

The drawings referred to in this description should not be understood as being drawn to scale unless specifically noted.

DESCRIPTION OF EMBODIMENTS

Various embodiments are described below, with reference to detailed illustrative embodiments, in the context of a single piece lead fixation device and methods of using such device. It will be apparent from the description provided herein that the systems, apparatuses and methods can be embodied in a wide variety of forms. Consequently, the specific structural and functional details disclosed herein are representative and do not limit the scope of embodiments of the present technology.

It should be noted that as used herein and in the appended claims, the singular forms "a," "an," and "the" include plural references unless the context clearly dictates otherwise. Thus, for example, reference to a "lead" is a reference to one or more leads and equivalents thereof known to those skilled in the art, and so forth. Unless defined otherwise, all technical and scientific terms used herein have the same meanings as commonly understood by one of ordinary skill in the art.

Existing lead fixation devices are comprised of two or more components and attach to the outside of the skull using neurosurgical screws. See, e.g., U.S. Pat. No. 4,328,813 to Ray for "Brain Lead Anchoring Systems" issued May 11, 1982; U.S. Pat. No. 5,927,277 to Baudino et al. for "Method and Apparatus for Securing Probes Within A Burr Hole" issued Jul. 27, 1999; U.S. Pat. No. 7,604,644 to Schulte et al. for "Apparatus for Securing a Therapy Device Within A Burr Hole" issued Oct. 20, 2009; U.S. Pat. No. 7,204,840 to Skakoon et al. for "Deep Organ Access Device and Method" issued Apr. 17, 2007; U.S. Patent Application Publication No. 2009/0306750 to Boling et al. for "Lead Fixation Assembly and Method of Using Same" published Dec. 10, 2009; U.S. Patent Application Publication No. 2009/0112327 to Lane et al. for "Burr Hole Plug Designs" published Apr. 30, 2009; and U.S. Patent Application Publication No. 2007/0233158 to Rodriquez for "Burr Hole Cap and Methods of Use" published Oct. 4, 2007, now U.S. Pat. No. 7,949,410, issued on May 24, 2011.

In brief, embodiments described herein disclose a single piece lead fixation device that is pressed directly into a standard sized burr hole and that does not require neurosurgical screws to secure it to the cranium. Embodiments enable the medical lead to be securely held in place in a retention track via an interference fit, using a combination of materials varying in stiffness. Further and as will be described herein, a longitudinal slit within the lead fixation device provides more positioning choices with regards to the medical lead (e.g., positioning the medical lead at an edge of the burr hole). Moreover, embodiments provide various devices and methods for securing retaining a seal in a burr hole, without using neurological screws.

Thus, embodiments of the single-piece lead fixation devices and methods described herein provide many clinical advantages, such as, but not limited to, the following: ease of implanting the device; low manufacturing cost leading to low retail cost; simplified single piece design; neueorsurgical screws are not necessary to secure the medical lead relative to the burr hole; improved patient comfort due to the softness of the rubber in the lead fixation devices; reduces risk of scalp erosion due to the softness of the rubber; and improved medical lead cushioning and reduced risk of damage because only the rubber contacts the medical lead.

Overview of Discussion

Example systems and methods of using a lead fixation device are described herein. The discussion that follows focuses on a description of an example lead fixation device for securing a medical lead in a burr hole and its method of use.

Example Lead Fixation Device

FIG. 1 is a perspective view of a lead fixation device 100, in accordance with an embodiment. In one embodiment, the lead fixation device 100 includes a single-piece structure. The single-piece structure includes a top surface 102, a bottom surface 114, an outer perimeter 116, and an inner perimeter 106, a central bore 110, and at least one retention tract, in one embodiment, the inner perimeter 106 includes a diameter 108 approximately equal to or smaller than a diameter of the burr hole 124 into which the lead fixation device 100 is designed to be deployed. The central bore 110 is located in approximately a center of the lead fixation device 100 and includes a central bore diameter.

Figure 2:
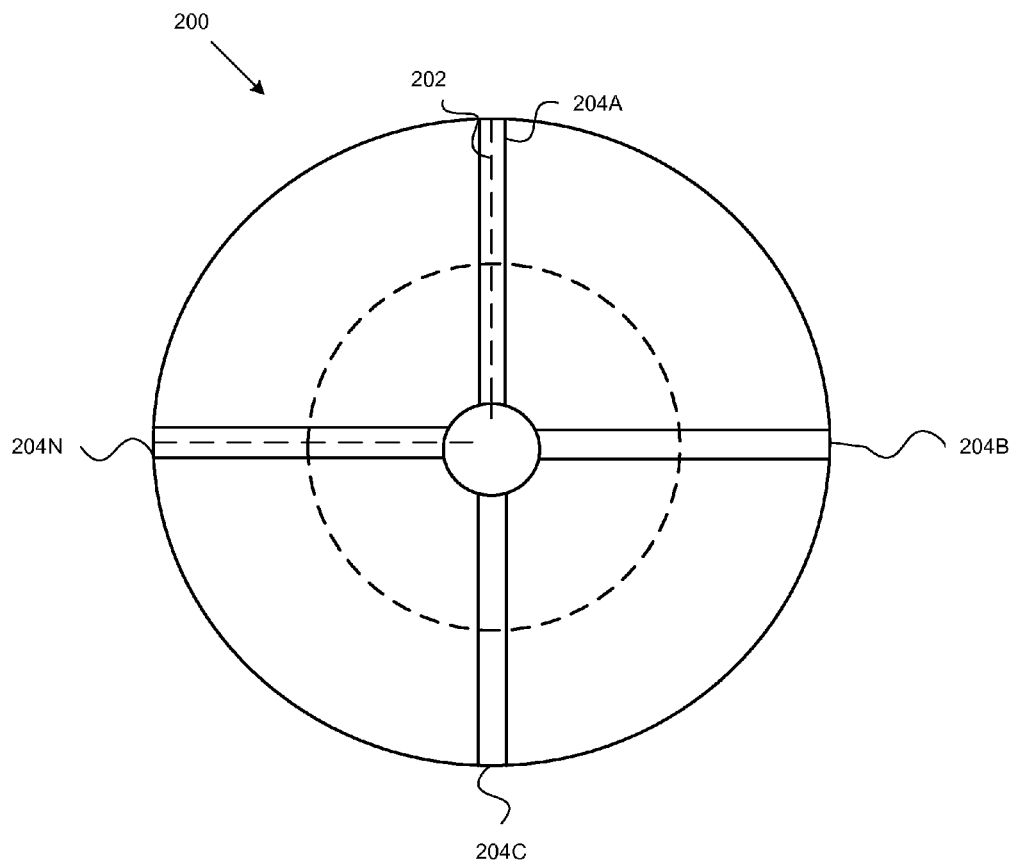
FIG. 2 is a perspective view from the top of a lead fixation device showing at least one retention tract, in accordance with an embodiment.

FIG. 2 is a perspective view from the top of a lead fixation device 200 showing at least one retention tract 204A, 204B, 204C and 204N (hereinafter, "retention tract 204"), in accordance with an embodiment. In one embodiment, the lead fixation device 200 is the same as that shown in FIG. 1. As seen in FIG. 2, the at least one retention tract formed in the top surface 102 of a cap 126 of the lead fixation device 100, the retention tract 204 for retaining, with an interference fit, a portion of a body of the medical lead 202 in the lead fixation device 200.

Further, as can be seen, multiple retention tracts may be made into the cap of the lead fixation device 200 to accommodate differing angles of installation relative to the desired lead location. Further, the diameter of the bore in the lead fixation device may be formed to be large enough to accommodate more than one lead body (e.g., a larger central bore may be made to accommodate two or more leads). Moreover, the lead fixation device may be provided with a slit to allow it to be pried open and the lead fixation device slid laterally onto (or away from) the implanted lead body. This would allow the option of situating the lead fixation device around the lead body (or pulling the lead fixation device off of the lead body) sideways instead of having to pass the lead fixation device over the entire proximal portion of the medical lead to insert it (or remove it).

Figure 3:
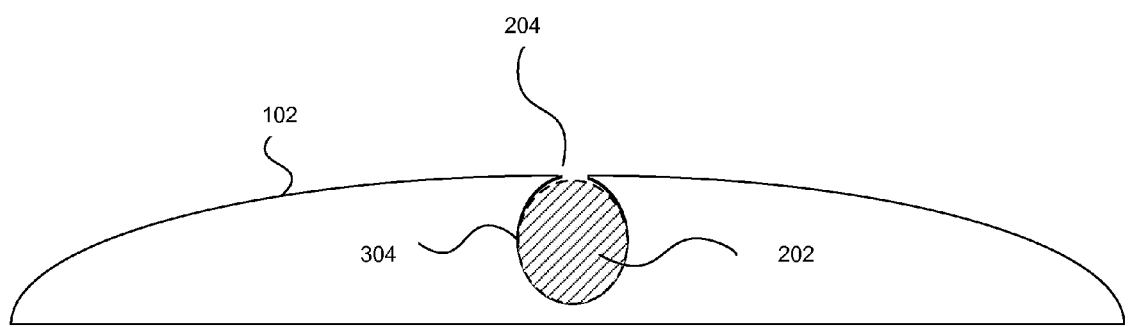
FIG. 3 is a perspective view of a medical lead within a trough of a retention tract, in accordance with an embodiment.

FIG. 3 is a perspective view of a medical lead 202 within a trough 304 of at least one retention tract 204, in accordance with an embodiment. In one embodiment, the trough 304 is formed in the top surface 102. The trough 304 includes a generally semicircular cross section having a radius approximating a radius of the body of the medical lead 202. In one embodiment, the trough 304 formed in the top surface 102 has a generally semicircular cross section. The generally semicircular cross section is characterized by a radius that is approximately equal to or slightly greater than the radius of the body of the medical lead and compressible from a first relaxed position to a second under tension position.

Referring to FIG. 1, in one embodiment, the portion of the central bore 110 includes a substantially circular perimeter. The term, "substantially circular", refers to a portion of the central bore 110 being circular or almost circular so as to appear more circular than any other shape. Further, in one embodiment, the single-piece structure is mushroomed-shaped, as shown in FIG. 1. In another embodiment, the diameter of the central bore 110 is larger than a diameter of the body of the medical lead.

Another embodiment includes at least one element for securing the lead fixation device 100 to the cranium of the human patient.

Figures 4A, 4B:
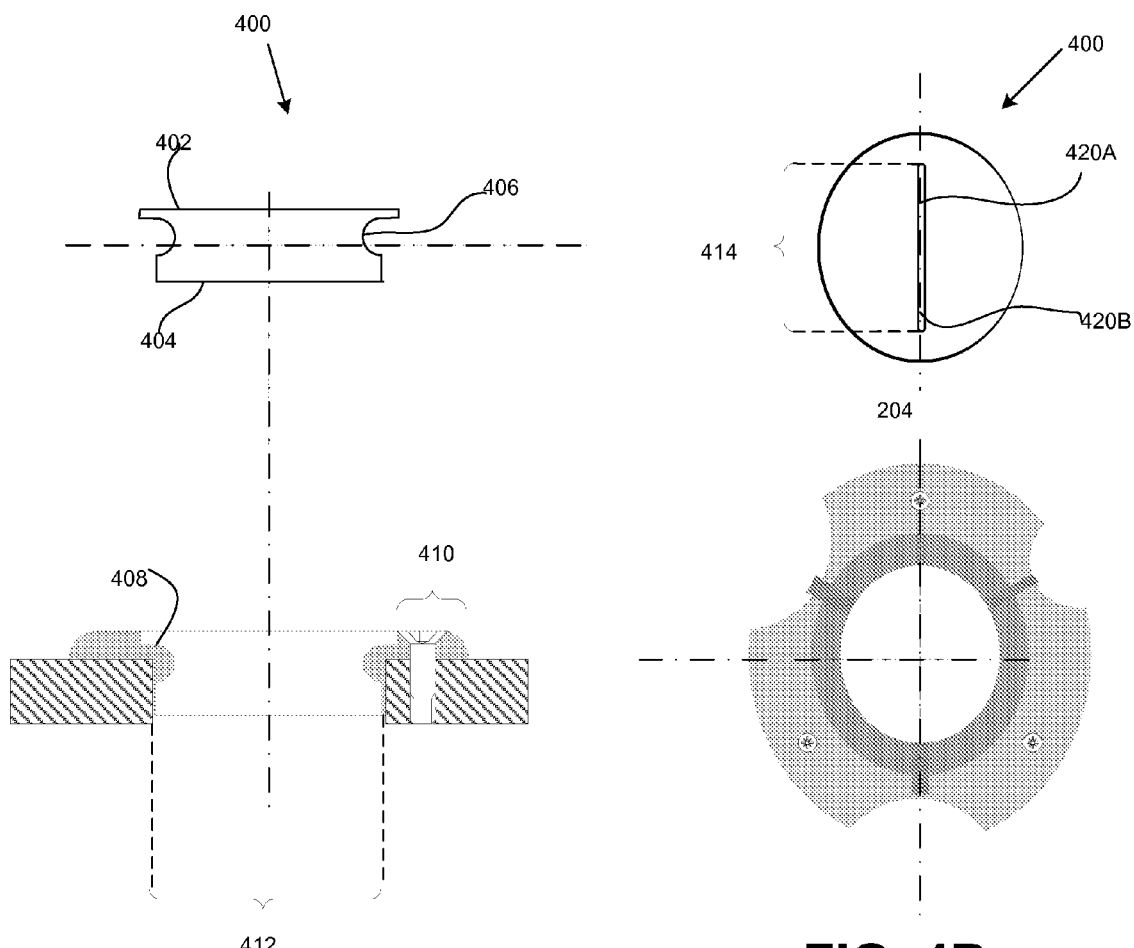
FIG. 4A is a side perspective view of a lead fixation device centered over a burr hole and a notch locking mechanism, in accordance with an embodiment.
FIG. 4B is a top perspective view of the lead fixation device showing a burr hole with a substantially rectangular perimeter centered over a notch locking mechanism, in accordance with an embodiment.

FIG. 4A is a side perspective view of a lead fixation device 400 centered over a burr hole and a notch locking mechanism, in accordance with an embodiment.

FIG. 4B is a top perspective view of the lead fixation device 400 showing a burr hole 412 with a substantially rectangular perimeter centered over a notch locking mechanism 410, in accordance with an embodiment. In one embodiment, the portion of the central bore 110 includes a substantially rectangular perimeter configured for enabling the body of the medical lead to be positioned such that the body has an interference fit with the smaller dimensions of the substantially rectangular perimeter. The term, "substantially rectangular" refers to a portion of the central bore 110 being rectangular, or almost rectangular (e.g., an oval). For example, and with reference to FIG. 4B, the central bore with a substantially rectangular perimeter has a length 414. The off-center position 420A and the off-center positions 420B are towards the outer edges of the lead fixation device 400.

The term, "substantially off-center of a center of the central bore" refers to the body of the medical lead being enabled to be positioned towards the edge of the burr hole, through the slit formed by the substantially rectangular central bore. It should be appreciated that the slit can be formed such that the center of the slit passes horizontally through the center of the central bore 110. However, in one embodiment, the slit can be formed such that the slit does not pass through the center of the central bore 110.

In one embodiment, the single-piece structure includes a notch receiving component 406 surrounding the outer perimeter of the lead fixation device 400, wherein the notch receiving component 406 is configured for receiving a notch 408 of a notch locking mechanism 410 fitted into the burr hole, whereupon in response to receiving the notch 408, the lead fixation device 400 becomes retainably secure within the burr hole 412. In one embodiment, the notch locking mechanism 410 is a subassembly of a snap-in locking mechanism that snaps into the burr hole 412 and retainably supports the lead fixation device 400.

Figure 5A:
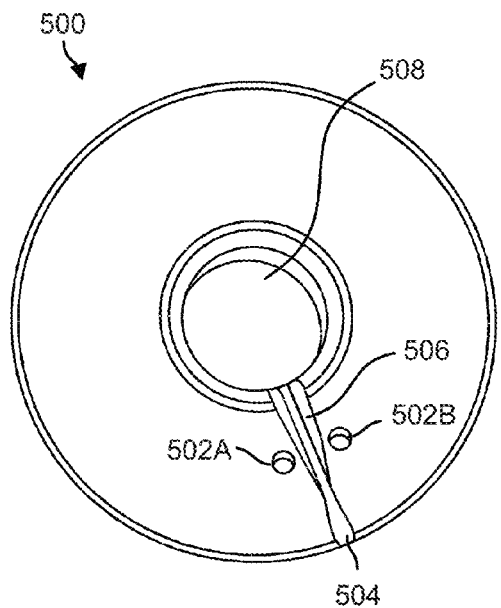
FIG. 5A is a top isometric view and FIG. 5B is a top perspective view of a lead fixation device showing two suture holes and a retention track, in accordance with an embodiment.
Figure 5B:
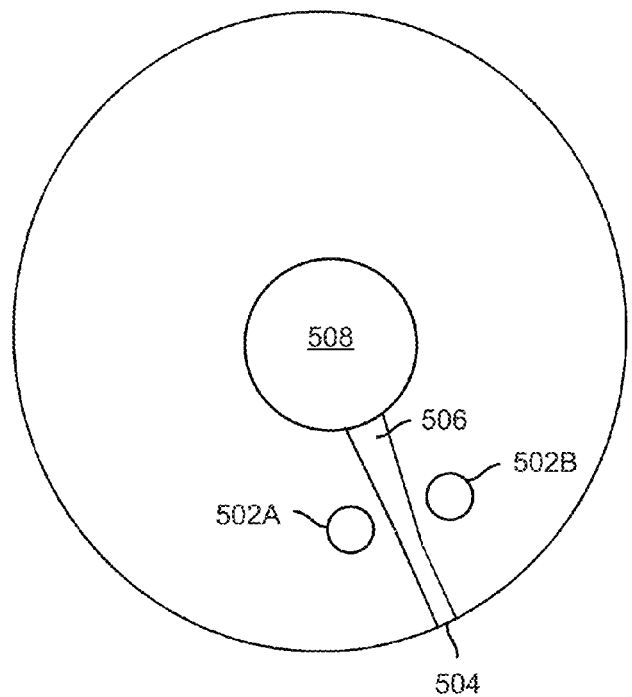

FIG. 5A is a top isometric view and FIG. 5B is a top perspective view of a lead fixation device 500 showing two suture holes 502A and 502B, and a retention track 504, in accordance with an embodiment. In one embodiment, the lead fixation device 500 includes a first suture aperture 502A on a first side of the trough 506, a second suture aperture 502B on a second side of the trough 506 approximately opposite the first suture aperture 502A. The first and second suture apertures, 502A and 502B, receive a suture extending through both the first and second suture apertures 502A and 502B.

In one embodiment and still referring to FIGS. 5A and 5B, the lead fixation device 500 includes a first suture aperture 502A, a second suture aperture 502B, each of the first and second suture apertures, 502A and 502B, respectively, having a diameter that is smaller than a diameter of the central bore 508. The first and second suture apertures 502A and 502B, respectively, extend through the top surface to the bottom surface and are disposed in the lead fixation device 500 on opposite sides of the trough 506. The first and second suture apertures, 502A and 502B, have a size and shape configured for accommodating at least one suture to secure the body of the medical lead in the lead fixation device 500.

Further, suture holes may be placed on either side of the retention tract. A non-absorbable piece of suture may be placed through these holes prior to placement of the lead fixation device. Once the medical lead is in position, the suture may be drawn tight and tied to aid in securing the medical lead relative to the lead fixation device.

Figure 6A:
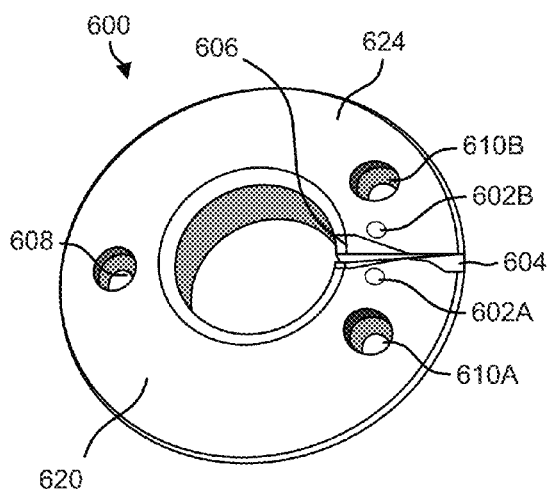
FIG. 6A is a top isometric view.
Figure 6B:
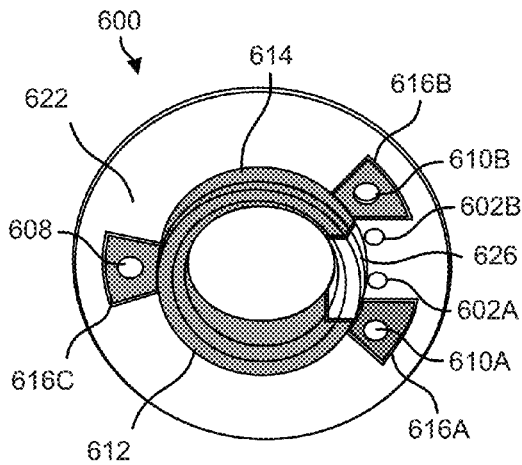
FIG. 6B is a bottom isometric view.
Figure 6C:
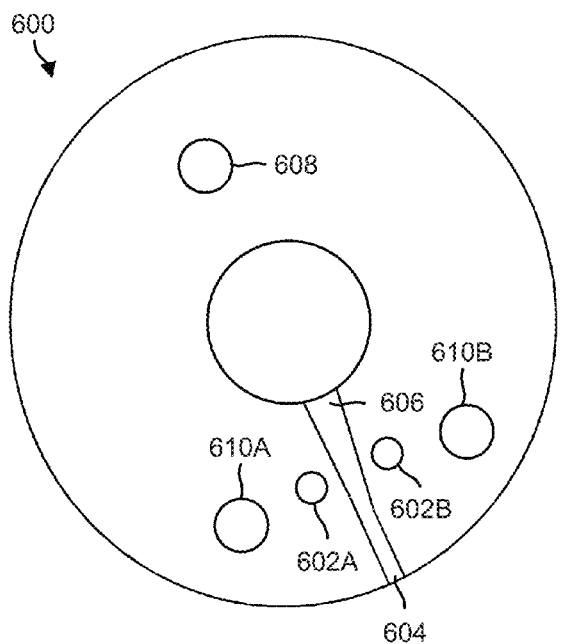
FIG. 6C is a top perspective view of a lead fixation device showing two suture holes, a retention track, suture apertures, and a screw aperture, in accordance with an embodiment.

FIG. 6A is a top isometric view, FIG. 6B is a bottom isometric view, and FIG. 6C is a top perspective view of a lead fixation device 600 showing two suture apertures 602A and 602B, a retention track 604, two forceps receptacles 610A, 610B and a screw aperture 608, in accordance with an embodiment. In one embodiment, the retention tract 604 includes a trough 606 formed in the top surface having a generally semicircular cross section, the general semicircular cross section having a radius that is approximately equal to or slightly greater than the radius of the body of the medical lead, a first forceps receptacle 610A disposed on a first side of the trough 606; and a second forceps receptacle 610E disposed on a second side of the trough 606 approximately opposite the first forceps receptacle. Further, in one embodiment, the lead fixation device 600 includes at least one screw aperture 608 extending from the top surface 620 through to the bottom surface 622 of the lead fixation device 600.

Figure 7:
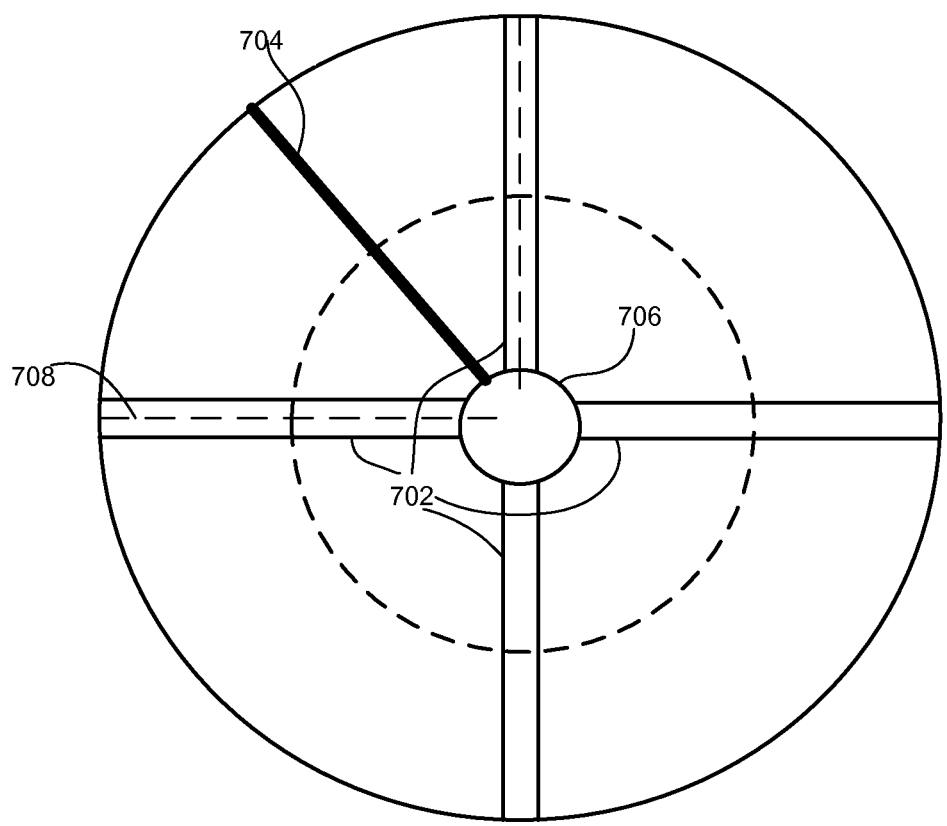
FIG. 7 is a top perspective view of a lead fixation device showing a plurality of retention tracks and a slit, in accordance with an embodiment.

FIG. 7 is a top perspective view of a lead fixation device 700 showing a plurality of retention tracks 702 and a slit 704, in accordance with an embodiment. In one embodiment, a slit 704 extending from the central bore 706 through a portion of the base and the cap to the outer perimeter. The slit 704 allows the lead fixation device 700 to be pried open temporarily to a degree sufficient to slide the lead fixation device 700 onto or off of the body of the medical lead 708.

In one embodiment, the single-piece structure of the lead fixation device, such as device 100 of FIG. 1, includes at least two integrally formed biocompatible materials, a first biocompatible material being substantially stiffer than a second biocompatible material and used to facilitate compression of the at least one retention tract from a relaxed position to an under tension position. For example, and referring to FIGS. 6A, 6B, and 6C, one embodiment of the lead fixation device 600 includes a C-shaped element 612 comprised of a stiff plastic. The C-shaped element 612 (shown in grey shade in FIGS. 6A and 6B) includes a C-shaped portion 614 and three tab-like elements 616A, 616B, 616C that extend outward from the C-shaped portion. The C-shaped portion 614 defines a first part of the base portion of the single piece structure. The tab-like elements 616A, 616B, 616C are provided with apertures 608, 610A, 610B extending through the single piece structure from the top surface 620 to the bottom surface 622. The rest of the lead fixation device 600 (shown in white in FIGS. 6A and 6B) includes a cap 624 and a second part 626 of the base portion 620 and may be comprised of a different, less stiff material than the material of the C-shaped element 612. The apertures 608, 610A, 610B defined in the tab-like elements 616A, 616B, 616C may be used to compress the lead fixation device at the time it is pressed into a burr hole. In one embodiment, the apertures 608, 610A, 610B in the tab-like elements 616A, 616B, 616C of the C-shaped element 612 may be designed to accommodate an arm of a forceps, so that a forceps can be used to provide a compressive force that causes two of the tab-like elements 616A and 616B to move toward each other, during insertion into the burr hole. When the surgeon is happy with the placement of the lead fixation device 600 in the burr hole, the surgeon can release the compressive force, allowing the lead fixation device to relax back towards its resting state and thus to encourage a tension fit of the lead fixation device in the burr hole. Screws may also then be placed in the same holes to fixate the lead fixation device to the cranium.

Example Method for Fixing a Medical Lead Relative to a Burr Hole Formed in a Human Patient Using a Lead Fixation Device A discussion of an example method for fixing a medical lead relative to a burr hole formed in a human patient using a lead fixation device follows.

Referring now to FIG. 1, it is shown that the lead fixation device 100 is passed over the distal end of the rigid insertion cannula 104 before the rigid annula is inserted into the brain.

Figure 8:
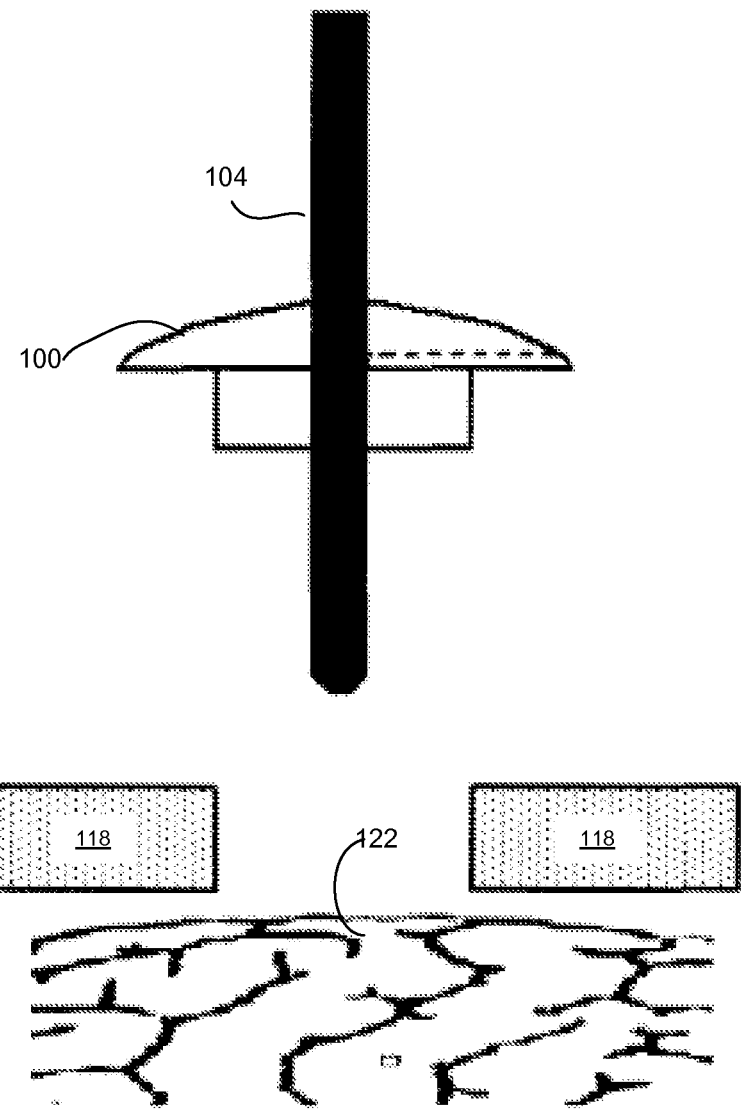
FIG. 8 is a side perspective view of a lead fixation device showing the lead fixation device being pulled proximally away from the skull over the rigid insertion cannula and out of the way of the insertion site, in accordance with an embodiment.

With reference to FIG. 8, a side perspective view of a lead fixation device showing the lead fixation device being pulled proximally away from the skull over the rigid insertion cannula and out of the way of the insertion site, is shown, in accordance with an embodiment.

As shown in FIG. 8, the lead fixation device is pulled proximally (away from the skull) over the rigid insertion cannula 104 and out of the way of the insertion site 122. If the diameter of the central bore in the lead fixation device is only slightly greater than the outer diameter of the cannula 104, the out-of-the way lead fixation device 100 may stay out of the way by virtue of frictional engagement of the cannula 104 and the lead fixation device 100. If the diameter of the central bore in the lead fixation device is not so close to the outer diameter of the cannula 104, the surgeon may choose to use a suture to keep the lead fixation device 100 out of the way of the lead insertion site 122 until the surgeon is happy with the position of the medical lead and ready to fix the lead in the lead fixation device 100.

Figure 9:
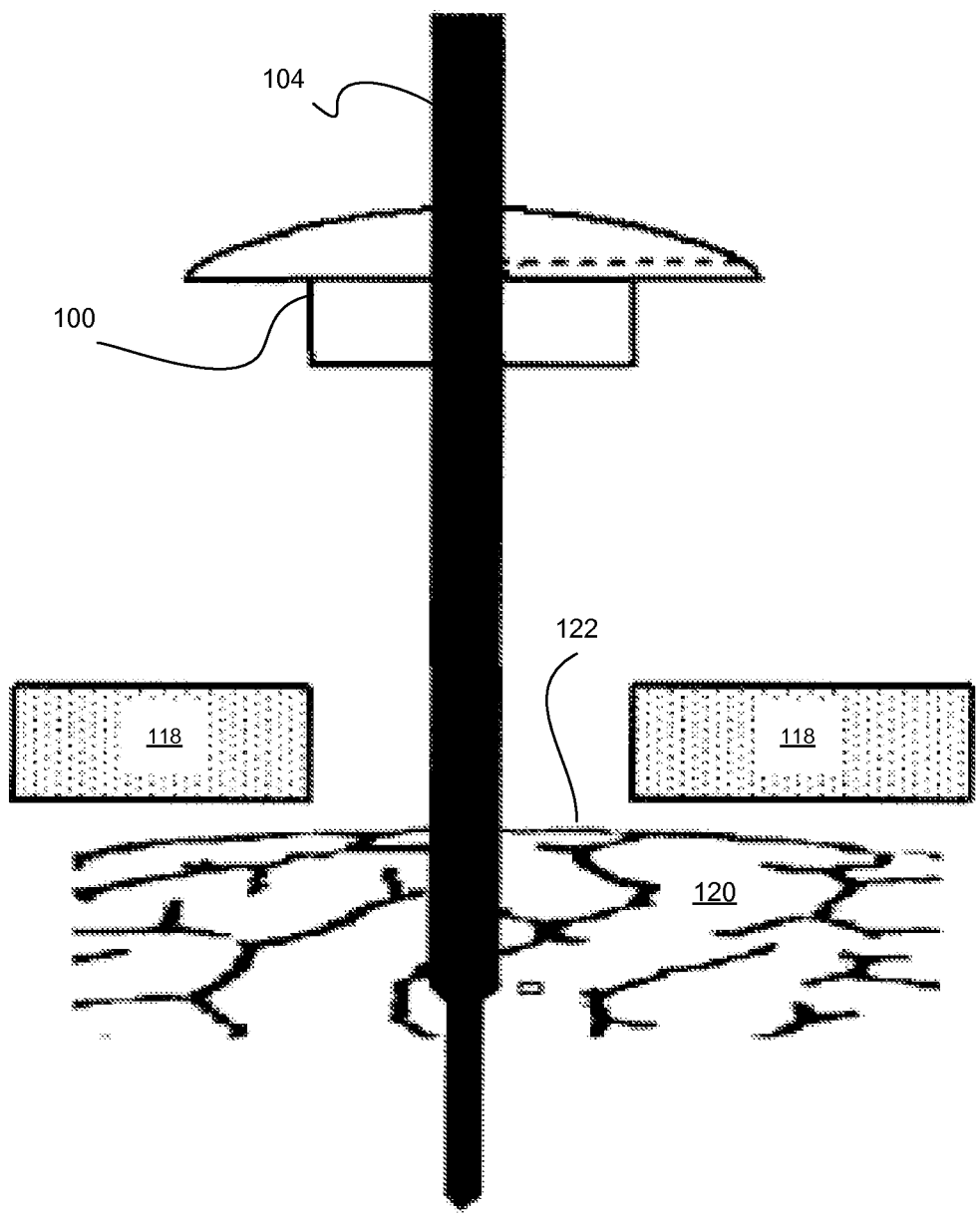
FIG. 9 is a side perspective view of a cannula and a lead fixation device being advanced into the brain, in accordance with an embodiment.

FIG. 9 is a side perspective view of a cannula 104 and a lead fixation device 122 being advanced into the brain 120, in accordance with an embodiment. As can be seen in FIG. 9, the insertion cannula 104 and medical lead are advanced into the brain 120 so that the distal end of the medical lead is positioned at the desired or target location.

Figure 10:
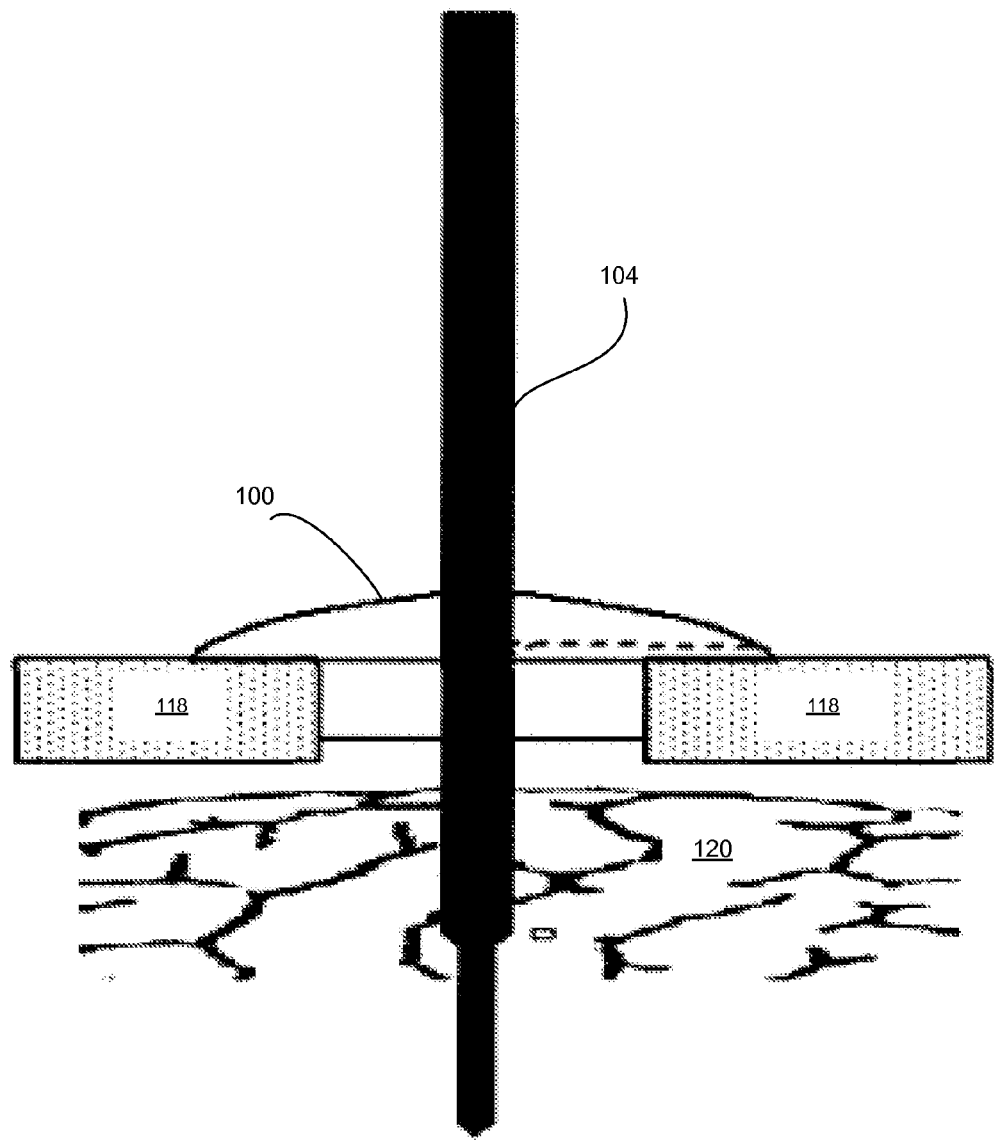
FIG. 10 is a side perspective view of the lead fixation device being pushed down into the burr hole, in accordance with an embodiment.

FIG. 10 is a side perspective view of the lead fixation device 100 being pushed down into the burr hole, in accordance with an embodiment. As can be seen, the lead fixation device 100 is pushed down into the burr hole.

Figure 11:
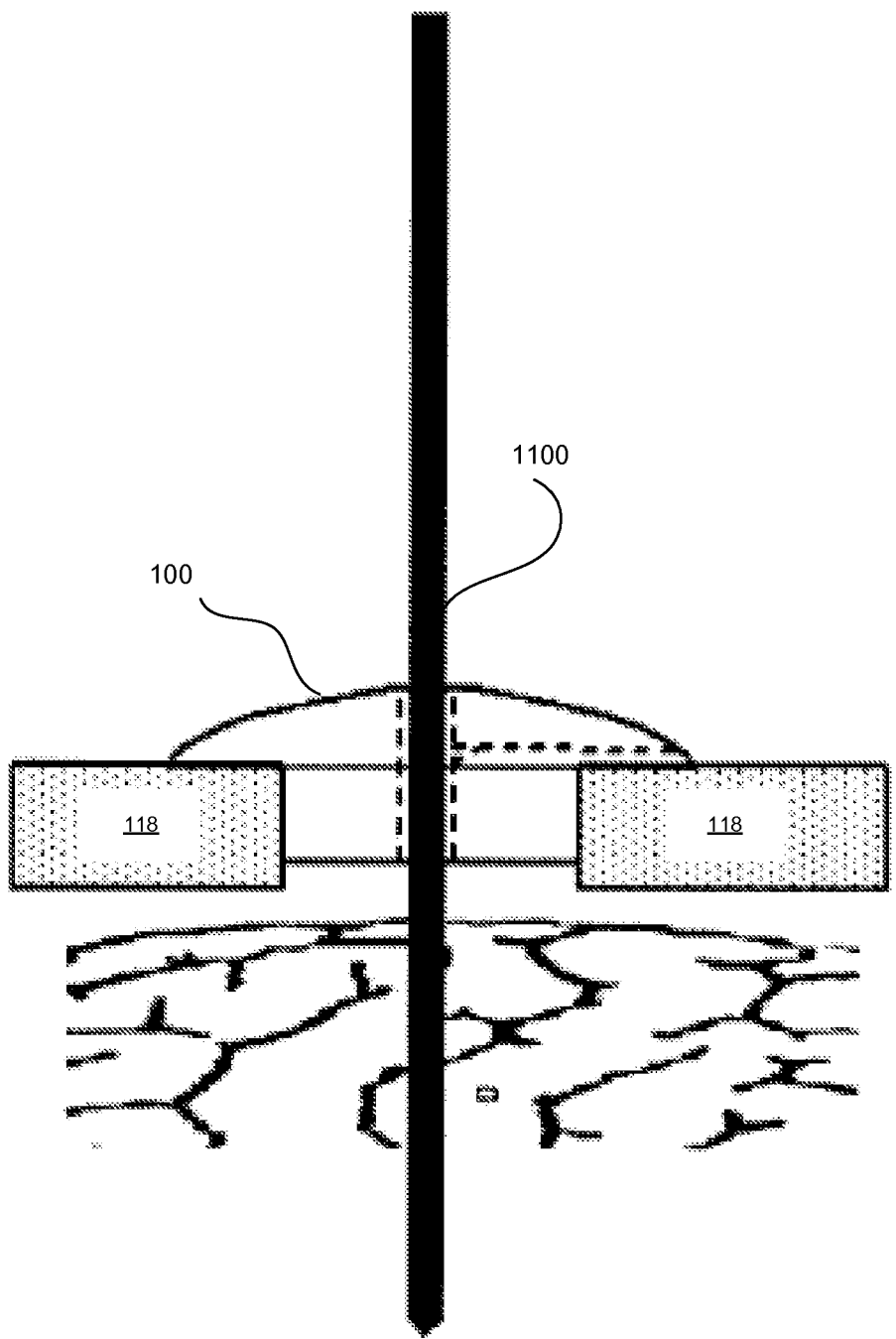
FIG. 11 is a side perspective view of the insertion cannula being withdrawn and the lead stylet being withdrawn, in accordance with an embodiment.

FIG. 11 is a side perspective view of the insertion cannula 104 being withdrawn and the lead stylet being withdrawn, in accordance with an embodiment. As can be seen in FIG. 11, the insertion cannula 104 is withdrawn and the lead stylet (previously placed in a lumen of the body of the medical lead 1100 to contribute stiffness to the medical lead 1100 while it is being positioned at the target location) is withdrawn.

Figure 12:
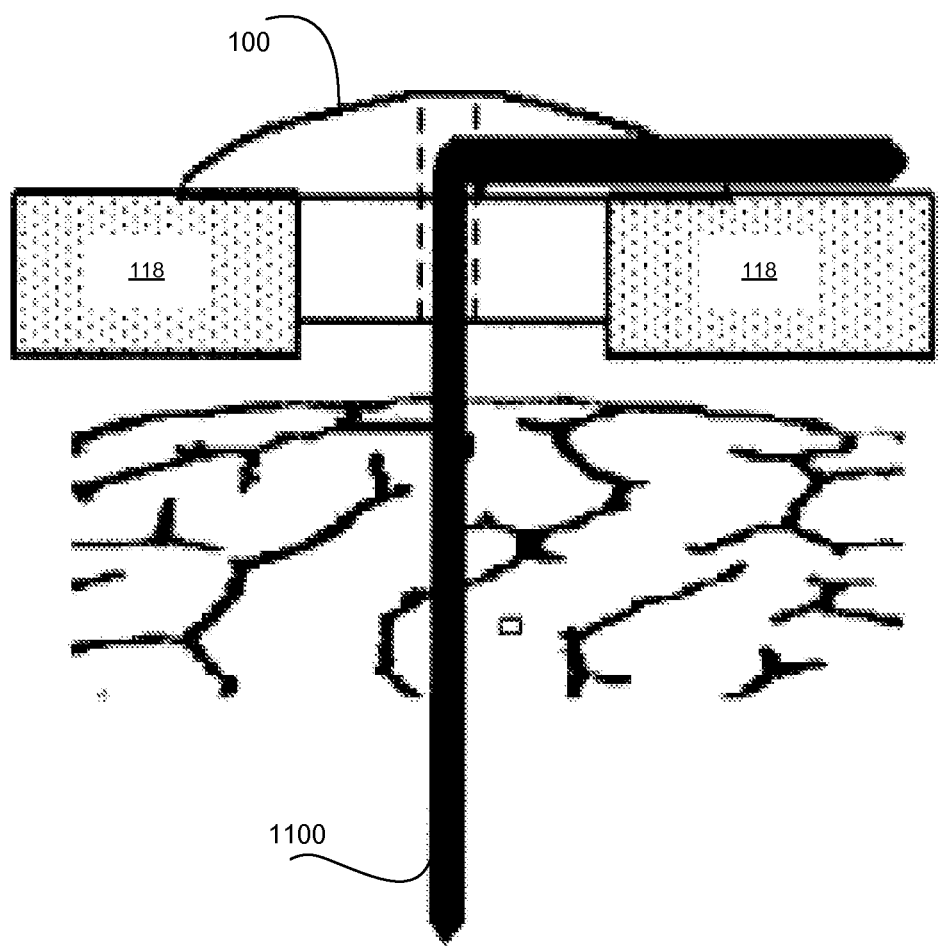
FIG. 12 is a side perspective view of lead fixation device being bent over and pushed into the retention tract, in accordance with an embodiment.

FIG. 12 is a side perspective view of lead fixation device being bent over and pushed into the retention tract, in accordance with an embodiment. As can be seen in FIG. 12, the medical lead 1100 is bent over and pushed into the lead fixation device 100 retention track (see 204 of FIG. 2) where a force fit secures the medical lead 1100.

Figure 13:
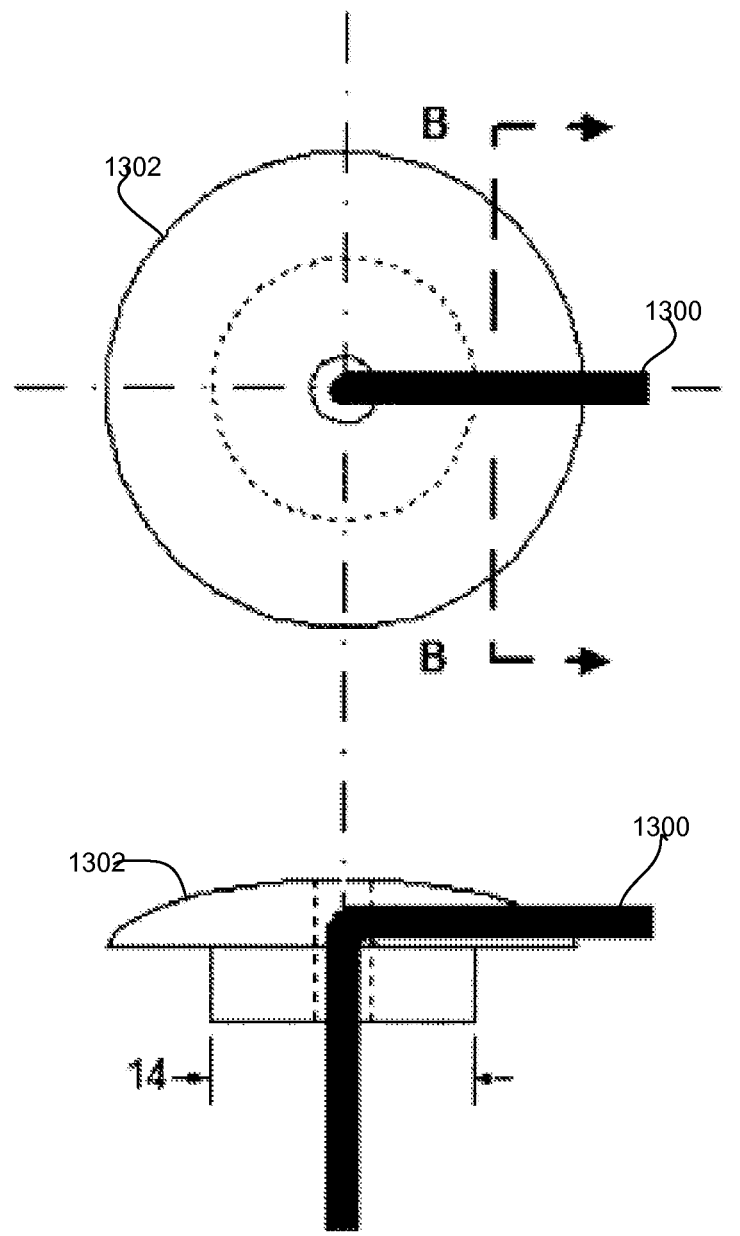
FIG. 13 is a top and side perspective view of an example of how a medical lead would be routed through the lead fixation device, in accordance with an embodiment.

FIG. 13 is a top and side perspective view of an example of how a medical lead 1300 would be routed through the lead fixation device 1302, in accordance with an embodiment.

Figure 14:
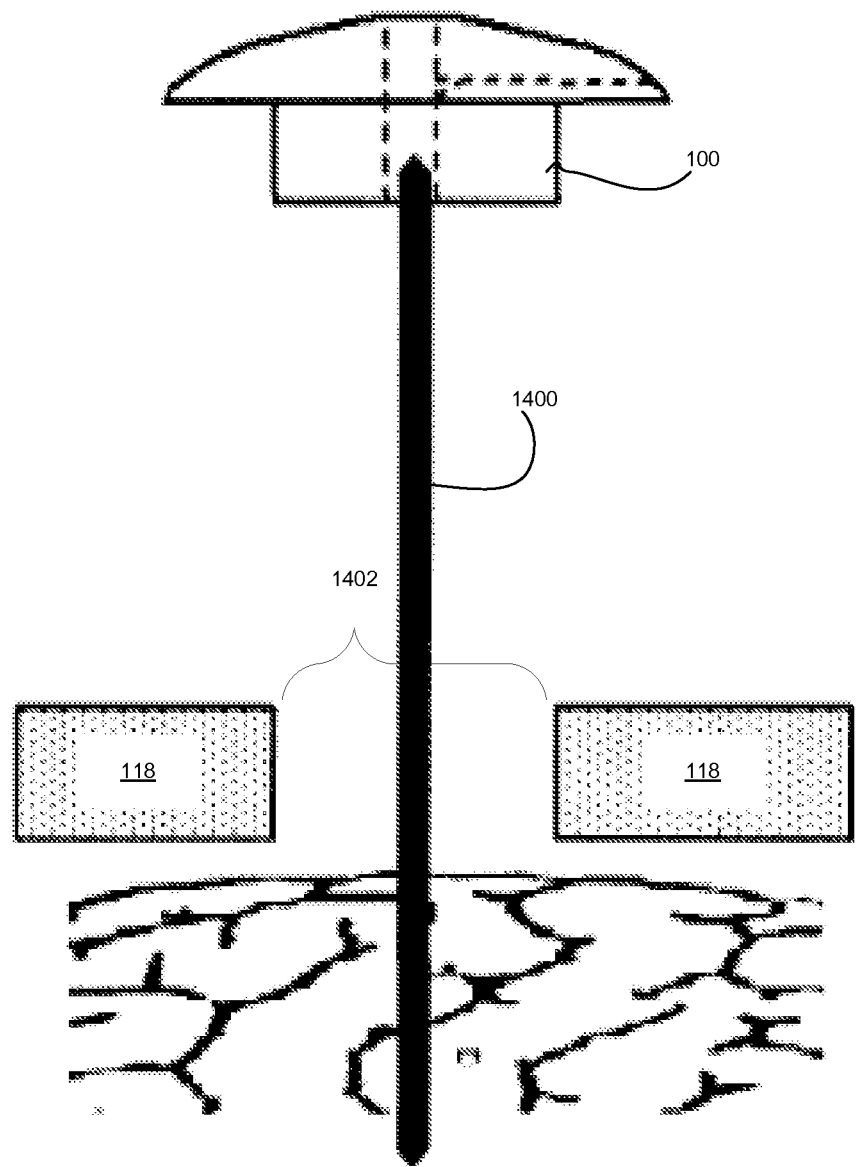
FIG. 14 is a side perspective view of a lead having a lead stylet inserted in a central lumen therein being inserted into a patient through a cannula inserted into a burr hole, in accordance with an embodiment.

FIG. 14 is a side perspective view of a medical lead having a lead stylet inserted in a central lumen therein being inserted into a patient through a cannula inserted into a burr hole 1402, in accordance with an embodiment. As shown, a medical lead having a lead stylet inserted in a central lumen therein is inserted into the patient through a cannula inserted into a burr hole 1402. Once the medical lead 1400 has been positioned where the surgeon wants it, insertion of the cannula and lead stylet are removed. The lead fixation device 100 then is passed over the proximal end of the medical lead 1400. Note that the hole through the lead fixation device 100 to accommodate the body of the medical lead 1400 is shown as being larger in diameter than the diameter of the body of the medical lead in FIG. 14.

Figure 15:
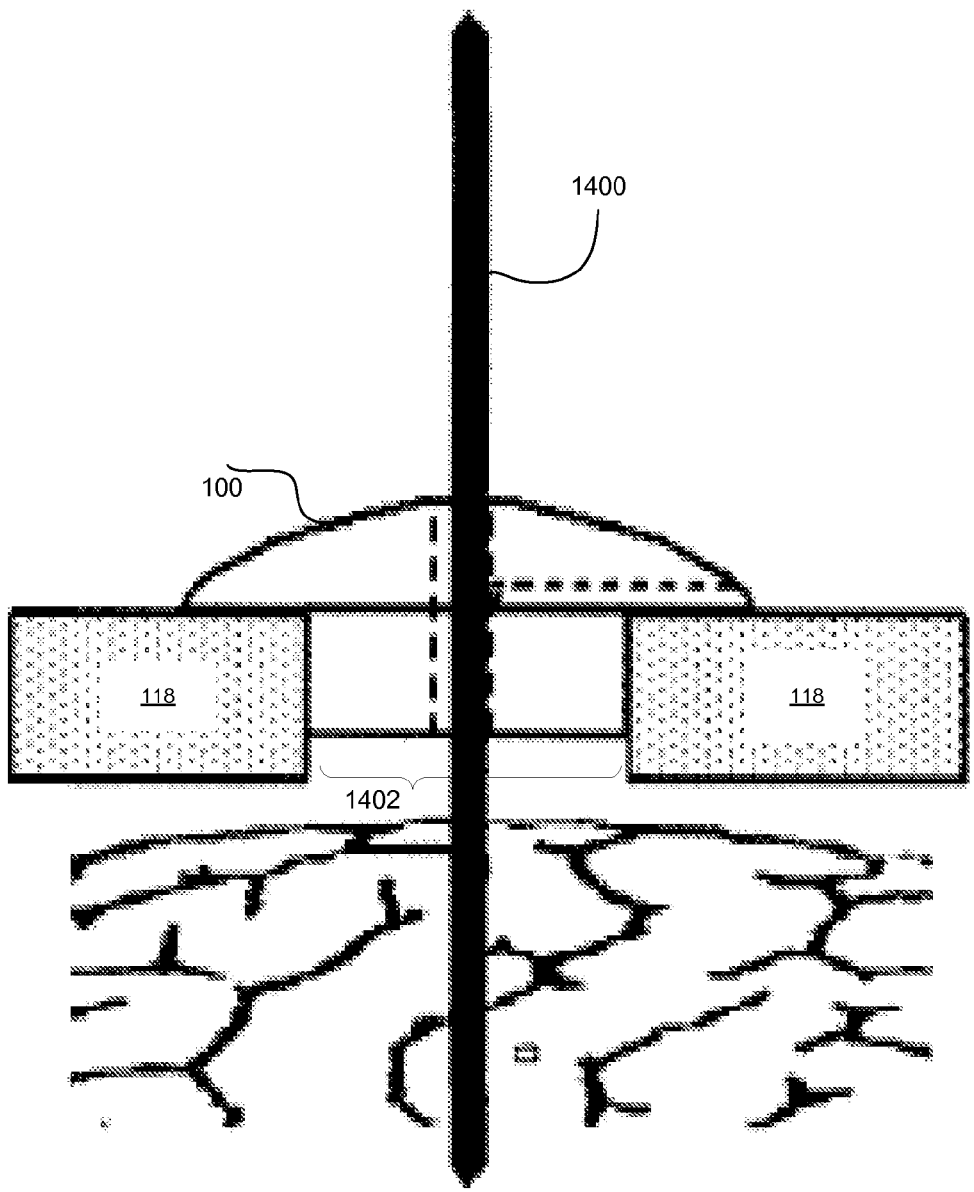
FIG. 15 is a side perspective view of a lead fixation device being passed over the medical lead and pressed into the burr hole, in accordance with an embodiment.

FIG. 15 is a side perspective view of a lead fixation device 100 being passed over the medical lead 1400 and pressed into the burr hole 1402, in accordance with an embodiment.

Figure 16:
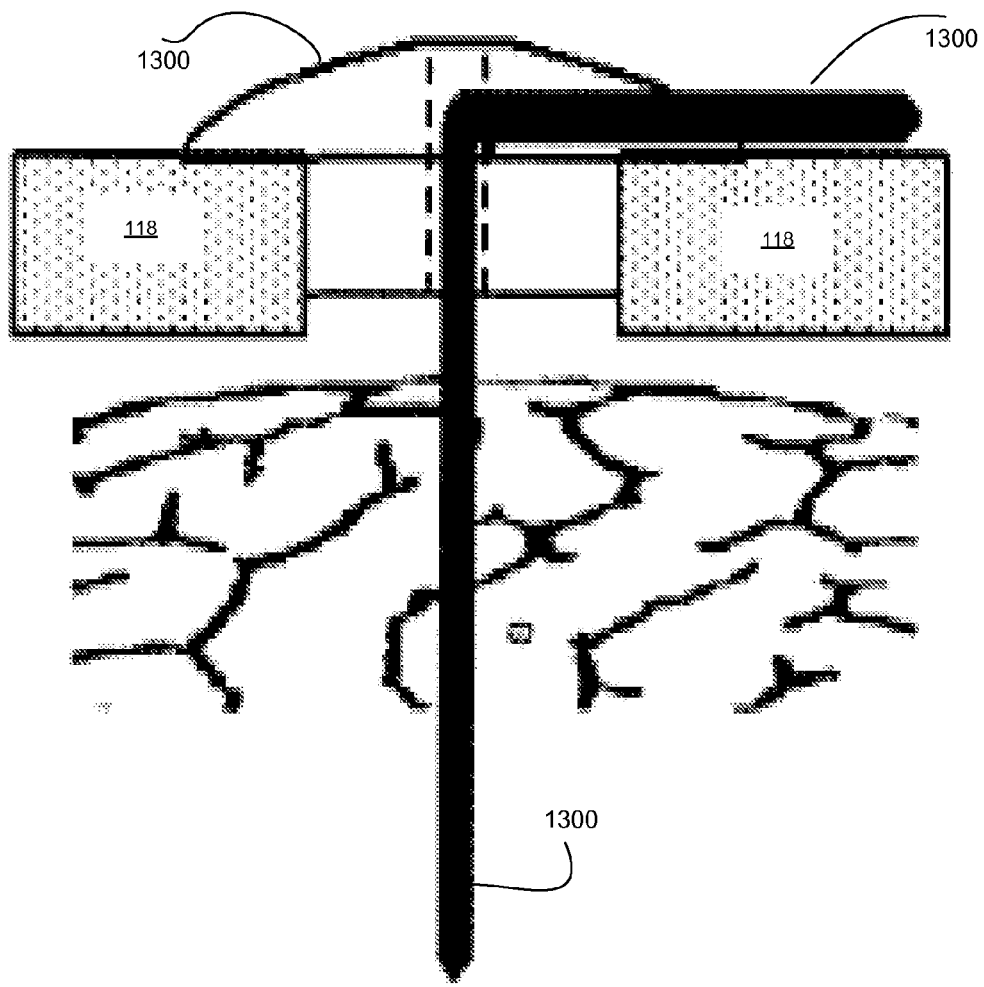
FIG. 16 is a side perspective view of a portion of a medical lead being bent over and pushed into the retention tract, in accordance with an embodiment.

FIG. 16 is a side perspective view of a portion of a medical lead 1499 being bent over and pushed into the retention tract (see 204 of FIG. 2), in accordance with an embodiment. As can be seen, a portion of the medical lead 1400 that extends proximally out of the lead fixation device 100 is bent over and pushed into the retention tract 1600, where a force fit secures the medical lead 1400.

Various example embodiments are thus described. All statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope, therefore, is not intended to be limited to the embodiments shown and described herein. Rather, the scope and spirit is embodied by the appended claims.

What is claimed is:

1. A lead fixation device for securing a medical lead in a human patient comprising:
 a single-piece structure comprised of at least two integrally formed biocompatible materials, a first biocompatible material being substantially stiffer than a second biocompatible material, the single-piece structure comprising:
  a cap having a top surface;
  a bottom surface;
  an outer perimeter; and
  an inner perimeter, the inner perimeter comprising a diameter approximately equal to or smaller than a diameter of a burr hole into which the lead fixation device is designed to be deployed;
  a central bore extending longitudinally from the top surface through to the bottom surface, a portion of the central bore being located in approximately a center of the lead fixation device and comprising a central bore diameter; and
  at least one retention tract formed in the cap, the retention tract extending generally radially outward from the central bore to the outer perimeter and having a maximum cross-section dimension and an opening at the top surface along the length of the retention track, the opening having a dimension substantially less than the maximum cross-section, the retention track configured for retaining a portion of a body of at least one medical lead in the lead fixation device, the retaining provided by an interference fit between the retention tract and the body,
 wherein a first portion of the single-piece structure comprising the at least one retention track and extending between the top surface and the bottom surface in a region of the at least one retention track is formed of the second biocompatible material to thereby facilitate compression of the first portion including the least one retention tract from a relaxed position to an under tension position.

2. The lead fixation device of claim 1, wherein each of the at least one retention tract comprises:
 a trough formed in the cap, the trough comprising a generally semicircular cross section having a radius approximating a radius of the body of the at least one medical lead.

3. The lead fixation device of claim 1, wherein the at least one retention tract comprises:
 a trough formed in the cap, the trough comprising a generally semicircular cross section, the generally semicircular cross section having a radius that is approximately equal to or slightly greater than a radius of the body of the at least one medical lead.

4. The lead fixation device of claim 3, further comprising:
 a first suture aperture on a first side of the trough; and
 a second suture aperture on a second side of the trough approximately opposite the first suture aperture, the first and second suture apertures configured for receiving a suture extending through both the first and second suture apertures.

5. The lead fixation device of claim 3, further comprising:
 a first suture aperture; and
 a second suture aperture, each of the first and second suture apertures having a diameter that is smaller than a diameter of the central bore, the first and second suture apertures extending through the top surface to the bottom surface and being disposed in the lead fixation device on opposite sides of the trough, the first and second suture apertures having a size and shape configured for accommodating at least one suture to secure the body of the at least one medical lead in the lead fixation device.

6. The lead fixation device of claim 3, further comprising:
a first suture aperture;
a first forceps receptacle disposed near a first side of the trough;
a second suture aperture;
a second forceps receptacle disposed near a second side of the trough; and
at least one screw aperture, each of the first and second suture apertures, the first and second forceps receptacles and the at least one screw aperture extending through the top surface to the bottom surface of the lead fixation device.

7. The lead fixation device of claim 1, wherein the at least one retention tract further comprises:
a trough formed in the cap having a generally semicircular cross section, the general semicircular cross section having a radius that is approximately equal to or slightly greater than the radius of the body of the at least one medical lead;
a first forceps receptacle disposed on a first side of the trough; and
a second forceps receptacle disposed on a second side of the trough approximately opposite the first forceps receptacle.

8. The lead fixation device of claim 7, further comprising:
at least one screw aperture extending from the top surface through to the bottom surface.

9. The lead fixation device of claim 1, wherein the portion of the central bore comprises a substantially circular perimeter.

10. The lead fixation device of claim 1, wherein the portion of the central bore comprises a substantially rectangular perimeter configured for enabling the body of the at least one medical lead to be positioned such that the body has an interference fit with a smaller dimension of the substantially rectangular perimeter.

11. The lead fixation device of claim 1, wherein the single-piece structure comprises:
a notch receiving component surrounding the outer perimeter of the lead fixation device, wherein the notch receiving component is configured for receiving a notch of a notch locking mechanism fitted into the burr hole, whereupon in response to receiving the notch, the lead fixation device becomes retainably secure within the burr hole.

12. The lead fixation device of claim 11, wherein the notch locking mechanism is a subassembly of a snap-in locking mechanism configured for snapping into the burr hole and retainably supporting the lead fixation device.

13. The lead fixation device of claim 1, further comprising:
a slit extending from the central bore through a portion of a base and the cap to the outer perimeter, the slit allowing the lead fixation device to be pried open temporarily to a degree sufficient to slide the lead fixation device onto or off of the body of the at least one medical lead.

14. The lead fixation device of claim 1, wherein the central bore diameter is larger than a diameter of the body of the at least one medical lead.

15. The lead fixation device of claim 1, further comprising:
at least one element for securing the lead fixation device to a cranium of the human patient.

16. A lead fixation device for securing a medical lead relative to a burr hole formed in a human patient comprising:
a single-piece structure formed from a first material and a second material, the first material having a stiffness that is greater than the stiffness of the second material, the single-piece structure comprising:
a cap formed of the second material, the cap having a top surface defining an outer perimeter of the single-piece structure, and at least one retention tract formed in the cap, the retention tract configured for retaining a portion of a body of the at least one medical lead in the lead fixation device, the retaining provided by an interference fit between the retention tract and the body; and
a base having a first portion formed of the first material, a second portion formed of the second material, and a bottom surface, the base defining an inner perimeter of the lead fixation device, the inner perimeter having a diameter approximately equal to or smaller than the diameter of a burr hole into which the lead fixation device is designed to be deployed, wherein the top surface extends between the inner perimeter and the outer perimeter;
wherein the cap and base together define a central bore extending longitudinally from the top surface through to the bottom surface, the central bore being located in approximately a center of the lead fixation device and having a generally circular perimeter, the central bore comprising a central bore diameter;
wherein the first portion of the base comprises an approximately C-shaped section partially defining both the central bore and the inner perimeter, and extending from the bottom surface towards the top surface; and
wherein the cap comprises a first tab extending outward from the approximately C-shaped section in a direction opposite the central bore, the first tab terminating between the inner perimeter and the outer perimeter and provided with an aperture or indentation.

17. The lead fixation device of claim 16, wherein the cap further comprises:
a second tab extending outward from the C-shaped section; and
a third tab extending outward from the C-shaped section, wherein each of the first, second and third tabs is provided with an aperture extending through the lead fixation device from the top surface through to the bottom surface, the first tab aperture configured for receiving an element for fixing the lead fixation device to a bone of the patient, the second tab aperture configured for receiving a first grasping end of a forceps, the third tab aperture configured for receiving a second grasping end of a forceps.

18. The lead fixation device of claim 16, further comprising:
a first suture aperture on a first side of the retention tract; and
a second suture aperture on a second side of the retention tract, the second suture aperture located approximately opposite the first suture aperture, the first and second suture apertures configured for receiving a suture extending through both suture holes.

19. A lead fixation device for securing a medical lead in a human patient comprising:
an assembly formed as a single-piece structure in a mushroom shape, the single piece structure comprised of at least two integrally formed biocompatible materials, a first biocompatible material being substantially stiffer than a second biocompatible material, the assembly comprising:
- a base having a bottom surface;
- a cap having a top surface;
- an inner diameter defined by the base and selected so that the base of the lead fixation device will fit securely in a burr hole formed in a cranium of the human patient;
- an outer diameter defined by the cap and selected to extend at least slightly beyond the diameter of the burr hole;
- a central bore extending longitudinally from the top surface through to the bottom surface, the central bore being located in approximately a center of the lead fixation device, the central bore comprising a generally circular perimeter and a central bore diameter, the central bore diameter being great enough to accommodate a diameter of bodies of at least two medical leads; and
- a plurality of retention tracts formed in the cap and extending generally radially outward from the central bore to the outer perimeter and having a maximum cross-section dimension and an opening at the top surface along the length of the retention track, the opening having a dimension substantially less than the maximum cross-section, the retention track configured for retaining a portion of each body of the bodies of the at least two medical leads in the lead fixation device, the retaining provided by an interference fit between the retention tract and the body, wherein a first portion of the single-piece structure comprising at least one of the plurality of retention tracts and extending between the top surface and the bottom surface in a region of the at least one of the plurality of retention tracks is formed of the second biocompatible material to thereby facilitate compression of the first portion including the least one of the plurality of retention tracts from a first relaxed position to a second under tension position.

* * * * *